United States Patent
Moffitt et al.

(10) Patent No.: US 8,909,337 B2
(45) Date of Patent: Dec. 9, 2014

(54) SYSTEM TO TREAT AV-CONDUCTED VENTRICULAR TACHYARRHYTHMIA

(75) Inventors: Julia Moffitt, Iowa City, IA (US); Andrew P. Kramer, Marine on St. Croix, MN (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 124 days.

(21) Appl. No.: 13/473,774

(22) Filed: May 17, 2012

(65) Prior Publication Data

US 2012/0232604 A1    Sep. 13, 2012

Related U.S. Application Data

(60) Continuation of application No. 12/473,783, filed on May 28, 2009, now Pat. No. 8,190,257, which is a division of application No. 11/099,226, filed on Apr. 5, 2005, now Pat. No. 7,555,341.

(51) Int. Cl.
| | |
|---|---|
| *A61N 1/365* | (2006.01) |
| *A61N 1/368* | (2006.01) |
| *A61N 1/362* | (2006.01) |
| *A61N 1/36* | (2006.01) |
| *A61N 1/39* | (2006.01) |
| *A61B 5/0464* | (2006.01) |
| *A61N 1/05* | (2006.01) |

(52) U.S. Cl.
CPC ............ *A61N 1/36114* (2013.01); *A61N 1/368* (2013.01); *A61N 1/3684* (2013.01); *A61B 5/0464* (2013.01); *A61N 1/3627* (2013.01); *A61N 1/3962* (2013.01); *A61N 2001/0585* (2013.01); *A61N 1/0587* (2013.01); *A61N 1/3622* (2013.01)

USPC ............ 607/9; 607/14; 607/37; 607/4; 607/7; 607/119; 607/148; 607/118

(58) Field of Classification Search
USPC ............ 607/14, 37, 4, 9, 7, 62, 118, 119, 148
See application file for complete search history.

(56) References Cited

U.S. PATENT DOCUMENTS

| | | | |
|---|---|---|---|
| 3,650,277 | A | 3/1972 | Sjostrand et al. |
| 4,628,942 | A | 12/1986 | Sweeney et al. |

(Continued)

FOREIGN PATENT DOCUMENTS

| | | | |
|---|---|---|---|
| EP | 0547734 A2 | 6/1993 | |
| EP | 1486232 A2 | 12/2004 | |

(Continued)

OTHER PUBLICATIONS

"U.S. Appl. No. 11/099,226, Final Office Action mailed Sep. 17, 2008", 9 pgs.

(Continued)

*Primary Examiner* — Christopher D Koharski
*Assistant Examiner* — Natasha Patel
(74) *Attorney, Agent, or Firm* — Schwegman Lundberg & Woessner, P.A.

(57) ABSTRACT

Various aspects of the present subject matter provide devices and methods to treat AV-conducted ventricular tachyarrhythmia (AVCVT). According to various embodiments of the method, an AVCVT is sensed, an IVC-LA fat pad is stimulated when the AVCVT is sensed to block AV conduction, and bradycardia support pacing is provided while the IVC-LA fat pad is stimulated. Other aspects and embodiments are provided herein.

20 Claims, 10 Drawing Sheets

(56) References Cited

U.S. PATENT DOCUMENTS

| | | | |
|---|---|---|---|
| 5,203,326 A | 4/1993 | Collins | |
| 5,243,980 A | 9/1993 | Mehra | |
| 5,330,507 A | 7/1994 | Schwartz | |
| 5,334,221 A | 8/1994 | Bardy | |
| 5,356,425 A | 10/1994 | Bardy et al. | |
| 5,411,531 A * | 5/1995 | Hill et al. | 607/14 |
| 5,507,784 A | 4/1996 | Hill et al. | |
| 5,651,378 A | 7/1997 | Matheny et al. | |
| 5,707,400 A | 1/1998 | Terry, Jr. et al. | |
| 5,713,924 A | 2/1998 | Min et al. | |
| 5,749,900 A | 5/1998 | Schroeppel et al. | |
| 5,792,187 A | 8/1998 | Adams | |
| 5,913,876 A | 6/1999 | Taylor et al. | |
| 6,144,878 A | 11/2000 | Schroeppel et al. | |
| 6,266,564 B1 | 7/2001 | Hill et al. | |
| 6,272,377 B1 | 8/2001 | Sweeney et al. | |
| 6,292,695 B1 | 9/2001 | Webster, Jr. et al. | |
| 6,308,104 B1 | 10/2001 | Taylor et al. | |
| 6,349,233 B1 | 2/2002 | Adams | |
| 6,381,499 B1 | 4/2002 | Taylor et al. | |
| 6,442,424 B1 | 8/2002 | Ben-Haim et al. | |
| 6,477,418 B2 | 11/2002 | Plicchi et al. | |
| 6,487,442 B1 | 11/2002 | Wood | |
| 6,571,121 B2 | 5/2003 | Schroeppel et al. | |
| 6,600,954 B2 | 7/2003 | Cohen et al. | |
| 6,668,191 B1 | 12/2003 | Boveja | |
| 6,690,971 B2 | 2/2004 | Schauerte et al. | |
| 6,735,471 B2 | 5/2004 | Hill et al. | |
| 6,778,854 B2 | 8/2004 | Puskas | |
| 6,845,267 B2 | 1/2005 | Harrison et al. | |
| RE38,705 E | 2/2005 | Hill et al. | |
| 6,904,318 B2 | 6/2005 | Hill et al. | |
| 6,912,419 B2 | 6/2005 | Hill et al. | |
| 6,934,583 B2 | 8/2005 | Weinberg et al. | |
| 6,937,896 B1 | 8/2005 | Kroll | |
| 7,277,761 B2 | 10/2007 | Shelchuk | |
| 7,542,800 B2 | 6/2009 | Libbus et al. | |
| 7,555,341 B2 | 6/2009 | Moffitt et al. | |
| 7,587,238 B2 | 9/2009 | Moffitt et al. | |
| 7,660,628 B2 | 2/2010 | Libbus et al. | |
| 7,769,450 B2 | 8/2010 | Libbus et al. | |
| 8,126,559 B2 | 2/2012 | Libbus | |
| 2002/0026222 A1 | 2/2002 | Schauerte et al. | |
| 2002/0032468 A1 | 3/2002 | Hill et al. | |
| 2002/0116030 A1 | 8/2002 | Rezai | |
| 2002/0161410 A1 | 10/2002 | Kramer et al. | |
| 2002/0183237 A1 | 12/2002 | Puskas | |
| 2002/0198570 A1 | 12/2002 | Puskas | |
| 2002/0198571 A1 | 12/2002 | Puskas | |
| 2003/0023279 A1 | 1/2003 | Spinelli et al. | |
| 2003/0036773 A1 | 2/2003 | Whitehurst et al. | |
| 2003/0040774 A1 | 2/2003 | Terry et al. | |
| 2003/0045914 A1 | 3/2003 | Cohen et al. | |
| 2003/0074039 A1 | 4/2003 | Puskas | |
| 2003/0181951 A1 | 9/2003 | Cates | |
| 2003/0229380 A1 | 12/2003 | Adams et al. | |
| 2004/0010303 A1 | 1/2004 | Bolea et al. | |
| 2004/0019364 A1 | 1/2004 | Kieval et al. | |
| 2004/0024422 A1 | 2/2004 | Hill et al. | |
| 2004/0030362 A1 | 2/2004 | Hill et al. | |
| 2004/0059383 A1 | 3/2004 | Puskas | |
| 2004/0111118 A1 | 6/2004 | Hill et al. | |
| 2004/0172074 A1 | 9/2004 | Yoshihito | |
| 2004/0172075 A1 | 9/2004 | Shafer et al. | |
| 2004/0186517 A1 | 9/2004 | Hill et al. | |
| 2004/0186531 A1 | 9/2004 | Jahns et al. | |
| 2004/0193231 A1 | 9/2004 | David et al. | |
| 2004/0199209 A1 | 10/2004 | Hill et al. | |
| 2004/0199210 A1 | 10/2004 | Shelchuk | |
| 2004/0215289 A1 | 10/2004 | Fukui | |
| 2004/0254616 A1 | 12/2004 | Rossing et al. | |
| 2005/0021092 A1 | 1/2005 | Yun et al. | |
| 2005/0065553 A1 | 3/2005 | Ben Ezra et al. | |
| 2005/0065575 A1 | 3/2005 | Dobak | |
| 2005/0075702 A1 | 4/2005 | Shafer | |
| 2005/0096705 A1 | 5/2005 | Pastore et al. | |
| 2005/0096707 A1 | 5/2005 | Hill et al. | |
| 2005/0131467 A1 | 6/2005 | Boveja | |
| 2005/0143412 A1 | 6/2005 | Puskas | |
| 2005/0143779 A1 | 6/2005 | Libbus | |
| 2005/0143785 A1 | 6/2005 | Libbus | |
| 2005/0143787 A1 | 6/2005 | Boveja et al. | |
| 2005/0149126 A1 | 7/2005 | Libbus | |
| 2005/0149127 A1 | 7/2005 | Libbus | |
| 2005/0149128 A1 | 7/2005 | Heil, Jr. et al. | |
| 2005/0149130 A1 | 7/2005 | Libbus | |
| 2005/0149131 A1 | 7/2005 | Libbus et al. | |
| 2005/0149132 A1 | 7/2005 | Libbus | |
| 2005/0149133 A1 | 7/2005 | Libbus et al. | |
| 2005/0149143 A1 | 7/2005 | Libbus et al. | |
| 2005/0149155 A1 | 7/2005 | Scheiner et al. | |
| 2005/0149156 A1 | 7/2005 | Libbus et al. | |
| 2005/0187584 A1 | 8/2005 | Denker et al. | |
| 2005/0187586 A1 | 8/2005 | David et al. | |
| 2005/0197600 A1 | 9/2005 | Schuler et al. | |
| 2005/0197675 A1 | 9/2005 | David et al. | |
| 2005/0261741 A1 | 11/2005 | Libbus et al. | |
| 2006/0079945 A1 | 4/2006 | Libbus | |
| 2006/0106429 A1 | 5/2006 | Libbus et al. | |
| 2006/0122675 A1 | 6/2006 | Libbus et al. | |
| 2006/0206153 A1 | 9/2006 | Libbus et al. | |
| 2006/0224202 A1 | 10/2006 | Moffitt et al. | |
| 2009/0234408 A1 | 9/2009 | Moffitt et al. | |

FOREIGN PATENT DOCUMENTS

| | | |
|---|---|---|
| EP | 1541193 A1 | 6/2005 |
| JP | 4862037 | 11/2011 |
| WO | WO-9216257 A1 | 10/1992 |
| WO | WO-9713550 A1 | 4/1997 |
| WO | WO-9740885 A1 | 11/1997 |
| WO | WO-0226318 A1 | 4/2002 |
| WO | WO-0226320 A1 | 4/2002 |
| WO | WO-0234327 A2 | 5/2002 |
| WO | WO-02085448 A2 | 10/2002 |
| WO | WO-03076008 A1 | 9/2003 |
| WO | WO-03082080 A2 | 10/2003 |
| WO | WO-03099377 A1 | 12/2003 |
| WO | WO-2004012814 A1 | 2/2004 |
| WO | WO-2004084990 A1 | 10/2004 |
| WO | WO-2004084993 A1 | 10/2004 |
| WO | WO-2004103455 A2 | 12/2004 |
| WO | WO-2004105870 A1 | 12/2004 |
| WO | WO-2004110549 A2 | 12/2004 |
| WO | WO-2004110550 A2 | 12/2004 |
| WO | WO-2005018739 A1 | 3/2005 |
| WO | WO-2005042091 A1 | 5/2005 |
| WO | WO-2005053788 A1 | 6/2005 |
| WO | WO-2005063332 A1 | 7/2005 |
| WO | WO 2005065771 A1 | 7/2005 |
| WO | WO-2006031331 A1 | 3/2006 |
| WO | WO-2006107578 A2 | 10/2006 |
| WO | WO-2006107578 A3 | 10/2006 |

OTHER PUBLICATIONS

"U.S. Appl. No. 11/099,226, Final Office Action mailed Oct. 25, 2007", 10 pgs.

"U.S. Appl. No. 11/099,226, Non Final Office Action mailed Apr. 3, 2007", 11 pgs.

"U.S. Appl. No. 11/099,226, Non-Final Office Action mailed Feb. 27, 2008", 8 pgs.

"U.S. Appl. No. 11/099,226, Notice of Allowance mailed Feb. 24, 2009", 6 pgs.

"U.S. Appl. No. 11/099,226, Response filed Jul. 30, 2007 to Non Final Office Action mailed Apr. 3, 2007", 14 pgs.

"U.S. Appl. No. 11/099,226, Response filed Jan. 21, 2009 to Final Office Action mailed Sep. 17, 2008", 16 pgs.

"U.S. Appl. No. 11/099,226, Response filed Jan. 22, 2008 to Final Office Action mailed Oct. 25, 2007", 16 pgs.

"U.S. Appl. No. 11/099,226 Response filed Jun. 25, 2008 to Non-Final Office Action mailed Feb. 27, 2008", 13 pgs.

(56) References Cited

OTHER PUBLICATIONS

"U.S. Appl. No. 12/473,783, Non Final Office Action mailed Aug. 22, 2011", 9 pgs.

"U.S. Appl. No. 12/473,783, Notice of Allowance Mailed Feb. 1, 2012", 8 pgs.

"U.S. Appl. No. 12/473,783, Response filed Nov. 22, 2011 to Non Final Office Action mailed Aug. 22, 2011", 9 pgs.

"European Application Serial No. 06739041.9, Office Action mailed Nov. 19, 2010", 4 pgs.

"European Application Serial No. 06739041.9, Response filed May 25, 2011 to Office Action mailed Nov. 19, 2011", 16 pgs.

"International Search Report and Written Opinion for Application No. PCT/US2006/010092, Date Mailed Sep. 26, 2006", 14 Pages.

"Japanese Application Serial No. 2008-505337, Amended Claims filed Feb. 25, 2009", 10 pgs.

Chapleau, M. W., et al., "Contrasting effects of static and pulsatile pressure on carotid baroreceptor activity in dogs", Circulation, vol. 61, No. 5, (Nov. 1987), 648-658.

Chapleau, Mark W., "Pulsatile activation of baroreceptors causes central facilitation of baroreflex", American Journal Physiol Heart Circ Physiol, (Jun. 1989), 256: H1735-1741.

Cooper, Terry B, et al., "Neural effects on sinus rate and atrioventricular conduction produced by electrical stimulation from a transvenous electrode catheter in the canine right pulmonary artery", Circulation Research, vol. 46, No. 1, (Jan. 1980), 48-57.

Janes, R. D., et al., "Anatomy of human extrinsic cardiac nerves and ganglia.", Am J. Cardiol., 57(4), (Feb. 1, 1986), 299-309.

Li, M., et al., "Vagal nerve stimulation markedly improves long-term survival after chronic heart failure in rats", Circulation, 109(1), (2004), 120-124.

Scherlag, B. J, et al., "Endovascular stimulation within the left pulmonary artery to induce slowing of heart rate and paroxysmal atrial fibrillation.", Cardiovasc Research, 54(2), (May 2002), 470-475.

Scherlag, M A., et al., "Endovascular Neural Stimulation Via a Novel Basket Electrode Catheter: Comparison of Electrode Configurations", Journal of Interventional Cardiac Electrophysiology, 4(1), (Apr. 2000), 219-224.

Thompson, Gregory W. "Bradycardia induced by intravascular versus direct stimulation of the vagus nerve", Annals of Thoracic Surgery, 65(3), (Mar. 1998), 637-642.

Zarse, Markus, et al, "Selective Increase of Cardiac Neuronal Sympathetic Tone—A Catheter-Based Access to Modulate Left Ventricular Contractility", Journal of the American College Cardiology, 46(7), (Oct. 4, 2005), 1354-1359.

Zhang, Y., et al., "Achieving regular slow rhythm during atrial fibrillation without atrioventricular nodal ablation: Selective vagal stimulation plus ventricular pacing", Deptt. of Cardiovascular Medicine, (Oct. 2004), 469-475.

\* cited by examiner

SYSTEM TO TREAT AV-CONDUCTED VENTRICULAR TACHYARRHYTHMIA

CLAIM OF PRIORITY

This application is a continuation of U.S. application Ser. No. 12/473,783, filed May 28, 2009, now issued as U.S. Pat. No. 8,190,257, which is a divisional of U.S. application Ser. No. 11/099,226, filed Apr. 5, 2005, now issued as U.S. Pat. No. 7,555,341, which are hereby incorporated by reference in their entirety.

TECHNICAL FIELD

This application relates generally to medical devices and, more particularly, to systems, devices and methods to treat AV-conducted ventricular tachyarrhythmias.

BACKGROUND

A supraventricular tachyarrhythmia (SVT) is an arrhythmia that originates from the supraventricular region, such as the atrium, the sinus node, the AV node or AV junction. Examples of SVT include atrial tachyarrhythmia as well as AV and AV Nodal Reentry Tachyarrhythmias (AVNRT). Atrial tachyarrhythmia includes atrial tachycardias such as atrial flutter, and further includes atrial fibrillation, for example. SVT can be conducted through the AV node, thus resulting in a ventricular tachyarrhythmia associated with the SVT. Ventricular tachyarrhythmias triggered by an SVT via conduction through the AV node are referred herein as AV-Conducted Ventricular Tachyarrhythmias (AVCVT).

Some SVTs are chronic in nature, whereas others are not chronic. The duration of these non-chronic SVTs can range from a time period of less than a minute to a time period of several days. An example of a non-chronic SVT is paroxysmal atrial tachycardia (PAT), which also may be referred to as paroxysmal SVT, AVNRT or AV reentry tachycardia. PAT is a type of rapid atrial arrhythmia characterized by brief periods of sudden-onset and often abrupt termination of atrial tachycardia. The sudden onset of the tachycardia is caused by micro-reentry within the AV node or macro-reentry between the AV node and a bypass tract, and can be associated with uncomfortable and annoying symptoms such as lightheadedness, chest pain, palpitations, anxiety, sweating and shortness of breath. An atrial tachycardia can evolve into more serious arrhythmias ventricular tachycardia.

Implanting a chronic electrical stimulator, such as a cardiac stimulator, to deliver medical therapy(ies) is known. Examples of cardiac stimulators include implantable cardiac rhythm management (CRM) devices such as pacemakers, implantable cardiac defibrillators (ICDs), and implantable devices capable of performing both pacing and defibrillating functions. However, some SVTs, such as PAT, can be difficult to treat because it typically is not considered to be lethal enough to warrant defibrillation shock treatment or surgical AV nodal ablation, which prevents the rapid ventricular heart rate associated with the SVT.

SUMMARY

Various aspects of the present subject matter relate to an implantable medical device. In various embodiments, the device comprises at least one port, a sensing circuit, a neural stimulation circuit, a pacing circuit and a controller. Each port is adapted to connect at least one lead that has at least one electrode. The sensing circuit is connected to the at least one port to sense at least one intrinsic signal for use in determining an AV-Conducted Ventricular Tachyarrhythmia (AVCVT) event. The neural stimulation circuit is connected to the at least one port to selectively apply a neural stimulation signal to an IVC-LA fat pad. The pacing circuit is connected to the at least one port to provide bradycardia support pacing to maintain at least a programmable minimum heart rate. The controller is connected to the sensing circuit, the neural stimulation circuit and the pacing circuit. The controller is adapted to determine the AVCVT event from the at least one intrinsic signal sensed by the sensing circuit, apply the neural stimulation signal to the IVC-LA fat pad during AVCVT event to block AV conduction to terminate the AVCVT event, and provide bradycardia support pacing when the neural stimulation signal is applied to the IVC-LA fat pad.

In various embodiments, the device includes a header, a right atrium detector, a right ventricle detector, a neural stimulator and a cardiac pacing stimulator. The header includes a first port to connect to a first lead with at least one electrode to be located to sense intrinsic signals from a right atrium, a second port to connect to a second lead with at least one electrode to be located to sense intrinsic signals from and provide electrical stimulation to a right ventricle, and at least a third port to connect to at least a third lead to be intravascularly inserted through a coronary sinus with at least one electrode located to sense intrinsic signals from and provide electrical stimulation to a left ventricle and at least one electrode located to stimulate an IVC-LA fat pad. The right atrium detector is connected to the first port of the header to sense an atrial rate based on intrinsic signals from the right atrium for use in determining an AV-Conducted Ventricular Tachyarrhythmia (AVCVT) event. The right ventricle detector is connected to the second port of the header to sense a ventricular rate based on intrinsic signals from the right ventricle for use in determining the AVCVT event. The neural stimulator is connected to the at least one third port of the header to selectively apply a neural stimulation signal to the IVC-LA fat pad during the AVCVT event to slow AV conduction and terminate the AVCVT event. The cardiac pacing stimulator is connected to the second port and the at least one third port to provide bradycardia support pacing to maintain at least a programmable minimum heart rate when the neural stimulation signal is applied to the IVC-LA fat pad and to provide biventricular pacing as part of a cardiac resynchronization therapy.

Various aspects of the present subject matter relate to a method to treat to treat AV-conducted ventricular tachyarrhythmia (AVCVT). According to various embodiments of the method, an AVCVT is sensed, an IVC-LA fat pad is stimulated when the AVCVT is sensed to block AV conduction, and bradycardia support pacing is provided while the IVC-LA fat pad is stimulated.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The following disclosure refers to paroxysmal atrial tachycardia (PAT) and AV nodal reentry tachycardia (AVNRT) as an example SVT. Those of ordinary skill in the art will understand, upon reading and comprehending this disclosure, how to treat AV-conducted ventricular tachyarrhythmia (AVCVT) associated with a variety of SVTs.

Cardiac Physiology

Figure 1A:
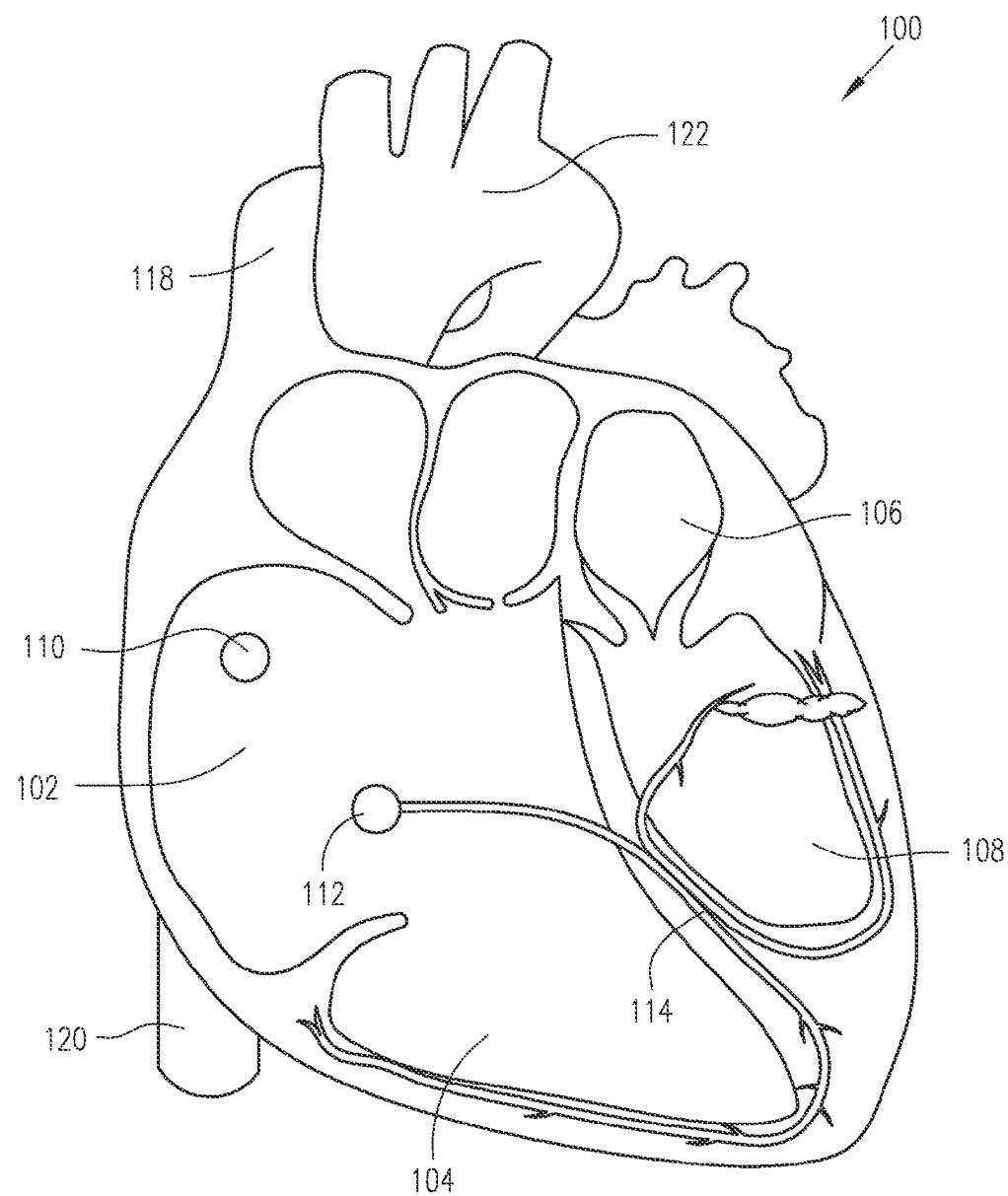
FIGS. 1A-1C illustrate a heart and are useful to illustrate the physiology associated with the electrical stimulation of the IVC-LA fat pad to selectively block AV conduction and terminate AV-conducted ventricular tachyarrhythmia (AVCVT) according to embodiments of the present subject matter.
Figure 1B:
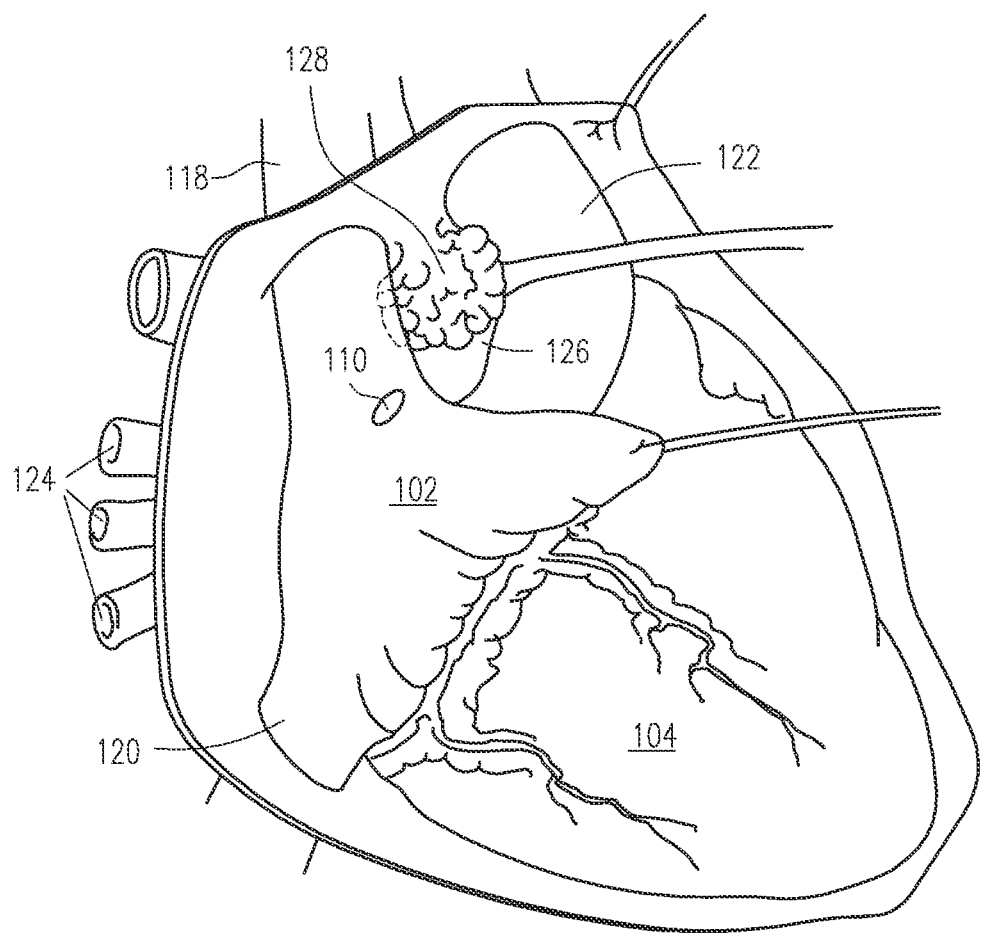
Figure 1C:
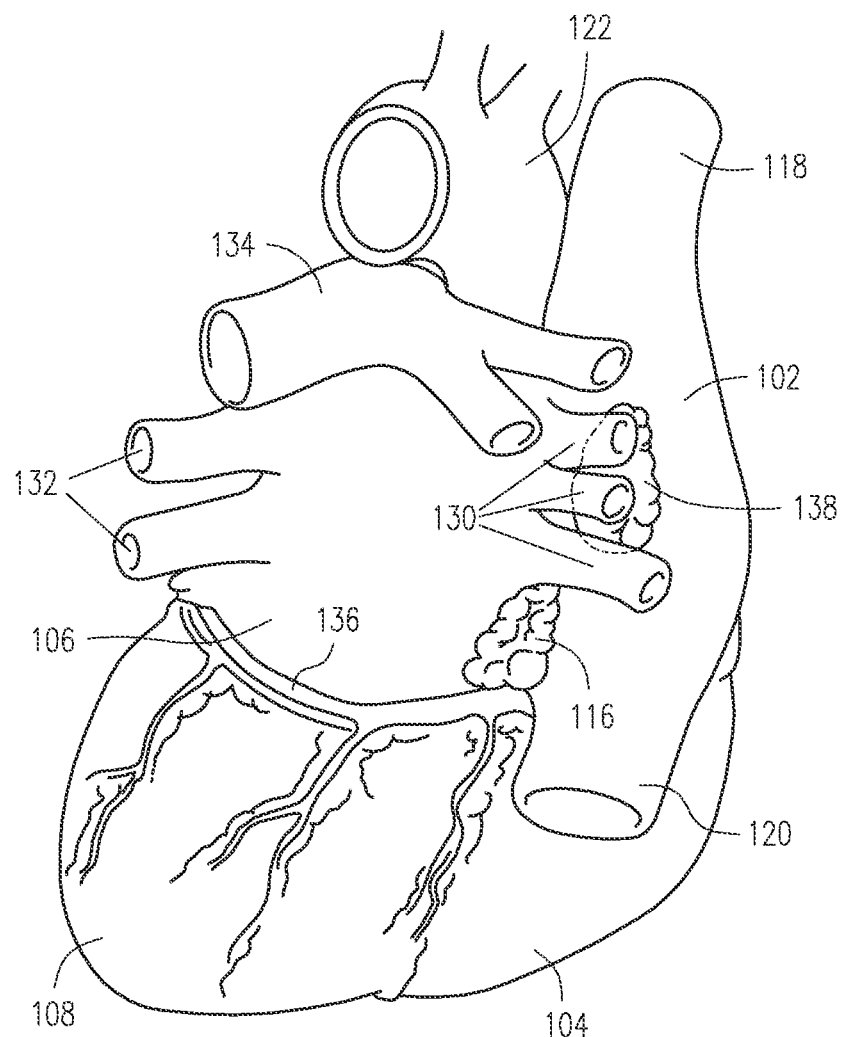

FIGS. 1A-1C illustrate a heart and are useful to illustrate the physiology associated with the electrical stimulation of the IVC-LA fat pad to selectively block AV conduction and terminate AVCVT according to embodiments of the present subject matter. The illustrated heart 100 includes a right atrium 102, a right ventricle 104, a left atrium 106 and a left ventricle 108. The illustrated heart 100 also includes a sinoatrial (SA) node 110 and an atrioventricular (AV) node 112. FIG. 1A illustrates the cardiac conduction system which controls heart rate. This system generates electrical impulses and conducts them throughout the muscle of the heart to stimulate the heart to contract and pump blood. The cardiac conduction system includes the SA node 110 and the AV node 112. The autonomic nervous system controls the firing of the SA node to trigger the start of the cardiac cycle. The SA node includes a cluster of cells in the right atrium that generates the electrical impulses. The electrical signal generated by the SA node moves from cell to cell down through the heart until it reaches the AV node 112, a cluster of cells situated in the center of the heart between the atria and ventricles. The AV node functions as an electrical relay station between the atria and the ventricles, such that electrical signals from the atria must pass through the AV node to reach the ventricles. The AV node slows the electrical current before the signal is permitted to pass down through to the ventricles, such that the atria are able to fully contract before the ventricles are stimulated. After passing the AV node, the electrical current travels to the ventricles along special fibers 114 embedded in the walls of the lower part of the heart.

The nervous system regulating the rhythm of the heart includes a number of ganglionated fat pads, including a fat pad associated with the SA node and a fat pad associated with the AV node. Stimulation of the fat pad associated with the SA node results in slowing of the sinus rate without prolonging AV conduction time, and stimulation of the fat pad associated with the AV node extends the AV conduction time without slowing of the sinus rate. Embodiments of the present subject matter selectively stimulate the fat pad associated with the AV node to provide an AV conduction block. The AV conduction block is reversible, as it exists for a time period corresponding to the time that the fat pad is stimulated.

FIGS. 1B and 1C illustrate other views a heart, including an IVC-LA fat pad 116 (a fat pad located between the inferior vena cava and the left atrium) that is electrically stimulated to selectively block the AV conduction according to embodiments of the present subject matter. FIGS. 1B and 1C illustrate the right side and left side of the heart, respectively. FIG. 1B illustrates the right atrium 102, right ventricle 104, SA node 110, superior vena cava 118, inferior vena cava 120, aorta 122, right pulmonary veins 124, and right pulmonary artery 126. FIG. 1B also illustrates a cardiac fat pad 128 between the superior vena cava and aorta. FIG. 1C illustrates the left atrium 106, left ventricle 108, right atrium 102, right ventricle 104, superior vena cava 118, inferior vena cava 120, aorta 122, right pulmonary veins 130, left pulmonary vein 132, right pulmonary artery 134, and coronary sinus 136. FIG. 1C also illustrates a cardiac fat pad 138 located proximate to the right cardiac veins and a cardiac fat pad 116 (also referred to herein as the IVC-LA fat pad) located proximate to or at the junction of the inferior vena cava and left atrium. Nerve endings in the IVC-LA fat pad 116 are stimulated in some embodiments using an electrode screwed into the fat pad using either an epicardial or intravascular lead, and are transvascularly stimulated in some embodiments using an intravascular electrode proximately positioned to the fat pad in a vessel such as the inferior vena cava 120 or coronary sinus 136 or a lead in the left atrium 106, for example.

Treatment of AV-Conducted Ventricular Tachyarrhythmia

Previously published data indicate that a 10V, 30 Hz, 0.05 ms bipolar electrical stimulation of the IVC-LA fat pad results in a selective increase in AV conduction time with minimal effects of sinus cycle length and atrial contractility.

The present subject matter effectively turns conduction through the AV node off and on at will by selectively stimulating the IVC-LA fat pad. The present subject matter provides a treatment of AV-conducted ventricular tachyarrhythmia (AVCVT) that includes stimulating autonomic ganglia in the fat pad associated with the AV node to selectively block conduction through the AV node and prevent fast ventricular rates associated with SVTs. Embodiments of the present subject matter sense an AVCVT induced by an SVT such as a PAT. In response, electrical stimulus is selectively delivered to the IVC-LA fat pad to selectively block AV conduction. Embodiments of the present subject matter sense an atrial tachycardia event (e.g. an atrial rate of approximately 160-200 bpm), and selectively stimulate the IVC-LA fat pad to selectively block AV conduction time to terminate the AVCVT. The delivery of the electrical stimulus to the IVC-LA fat pad is controlled to continue the AV conduction block until the triggering SVT stops and a normal sinus rhythm (NSR) is sensed. A triggering SVT can revert to a NSR on its own. A triggering AVNRT can be terminated by the AV conduction block provided by the neural stimulation of the autonomic ganglia in the AV-LA fat pad. Ventricular rate support is provided during the AV-conduction block to maintain an appropriate ventricular rhythm.

In an embodiment, when a PAT is sensed, the IVC-LA fat pad is electrically stimulated at a magnitude determined by closed-loop control using sensed cardiac intrinsic signals to terminate the PAT. In various embodiments, a pacemaker supports the ventricular rate by appropriately pacing the right ventricle when the AV conduction is inhibited. After the device detects that the atrial tachyarrhythmia has terminated, the electrical stimulation of the IVC-LA fat pad stops, thus providing a closed loop pacing system.

Various implantable device embodiments are used solely to terminate the AVCVT. These embodiments can use a relatively small battery to power the device because the stimulation is provided only during episodes of atrial tachycardia or other SVT that induced ventricular arrhythmia via conduction through the AV node. Various embodiments of the present subject matter use a pacemaker with an implantable stimulation electrode to selectively stimulate the nerves at the IVC-LA fat pad. In various embodiments, the electrode is placed on the epicardial surface of the heart at the IVC-LA fat pad. In various embodiments, the electrode is positioned within the coronary sinus to transvascularly stimulate the IVC-LA fat as part of a complete percutaneous implant. Thus, in comparison to defibrillation shocks and surgical ablation, the present subject matter provides a less invasive and effective treatment for PAT. Furthermore, with respect to AV surgical ablation, the present subject matter provides a temporary and reversible AV block. Thus, the present subject matter is well-suited to treat temporary arrhythmic episodes with a temporary AV block. Additionally, stimulating the IVC-LA fat pad rather than a vagus nerve trunk selectively provides the AV block without causing other unintended consequences that can occur if the vagus nerve trunk is stimulated.

Device Embodiments and Lead Positions

Figure 2A:
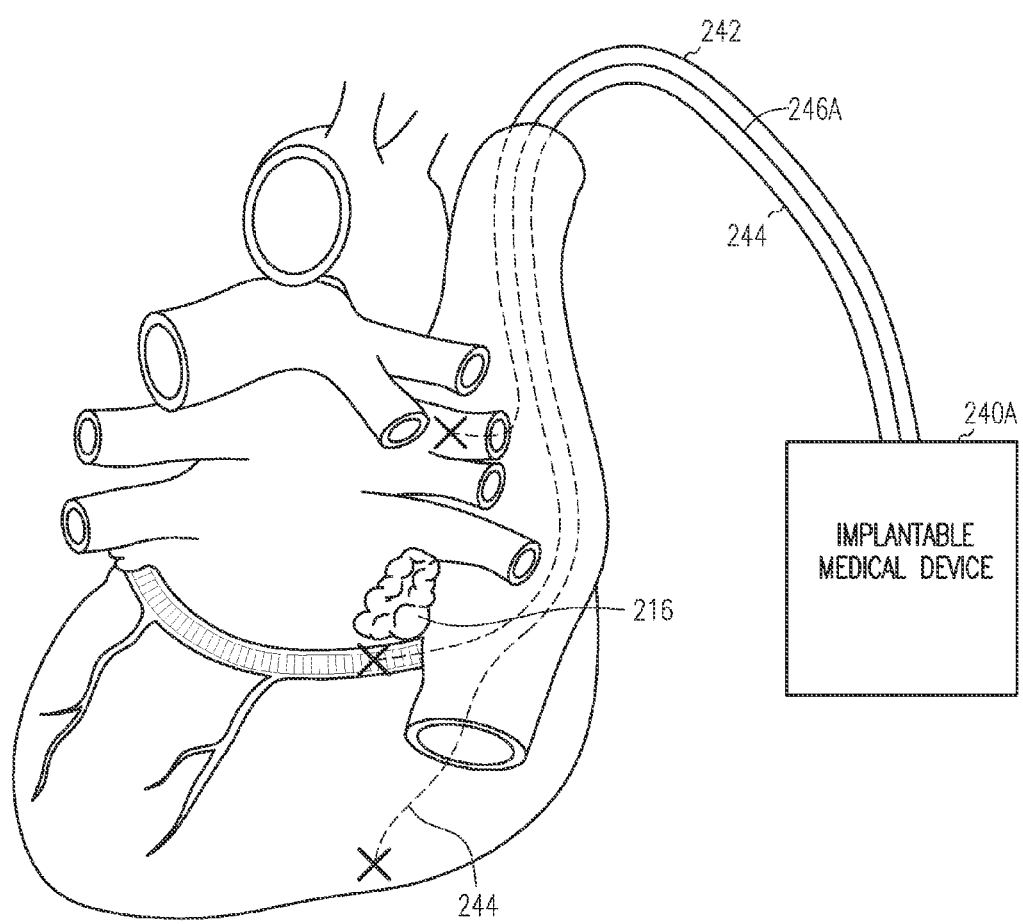
FIGS. 2A and 2B illustrate various embodiments of an implantable medical device and lead positions used to detect an AVCVT induced by an SVT, apply neural stimulation to the IVC-LA fat pad to selectively and temporarily block the AV conduction during the SVT to terminate and/or prevent the AVCVT, and provide bradycardia support pacing when the neural stimulation is applied and the AV conduction is inhibited.
Figure 2B:
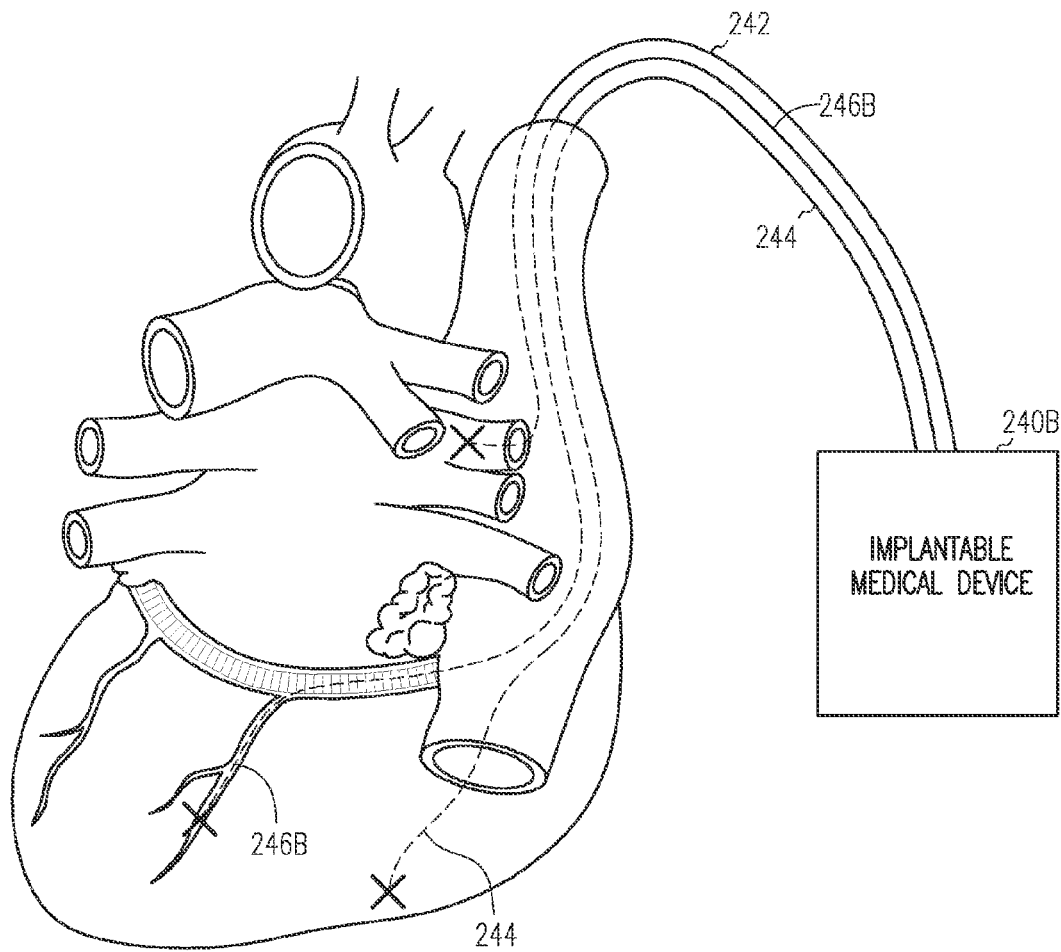

FIGS. 2A and 2B illustrate various embodiments of an implantable medical device and lead positions used to detect an AVCVT induced by an SVT, apply neural stimulation to the IVC-LA fat pad to selectively and temporarily block the AV conduction during the SVT to terminate and/or prevent the AVCVT, and provide bradycardia support pacing when the neural stimulation is applied and the AV conduction is inhibited.

In FIG. 2A, the illustrated implantable medical device 240A has three leads. A first lead 242 is placed in or proximate to the right atrium to detect intrinsic signals indicative of an atrial rate, which is capable of being used to determine a SVT event such as a PAT event. A second lead 244 is placed in or proximate to the right ventricle to pace the right ventricle, and detect intrinsic signals indicative of ventricular rate, which is capable of being used to determine AVCVT. The third lead 246A is placed proximate to the IVC-LA fat pad 216 to apply neural stimulation to the IVC-LA fat pad. Various embodiments use epicardial leads; various embodiments use intravascularly-fed leads; and various embodiments use various combinations of epicardial and intravascularly-fed leads. Thus, in an embodiment, the first, second and third leads are intravascularly inserted through a peripheral vein into the right atrium, and the first lead terminates therein. The second lead continues from the right atrium through the tricuspid valve into the right ventricle of the heart and terminates therein at a position to pace the right ventricle. The third lead enters the coronary sinus to intravascularly place an electrode therein and transvascularly stimulate the IVC-LA fat pad.

FIG. 2B is similar to FIG. 2A. However, in FIG. 2B, the third lead 246B for the device 240B extends further into the coronary sinus to place an electrode to pace the left ventricle. In various embodiments, one lead, such as the illustrated third lead, is used to stimulate the IVC-LA fat pad and to pace the left ventricle. In various embodiments, one lead is inserted into the coronary sinus to stimulate the IVC-LA fat pad and a second lead is used to pace the left ventricle. Such a system as is illustrated in FIG. 2B can be used to provide cardiac resynchronization therapy (CRT), which is discussed below.

Implantable cardiac devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. AV conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the SA node to the atrial myocardium, to the AV node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified AV delay interval with respect to the detection of an intrinsic atrial contraction or delivery of an atrial pace.

Implantable Medical Device

Figure 3:
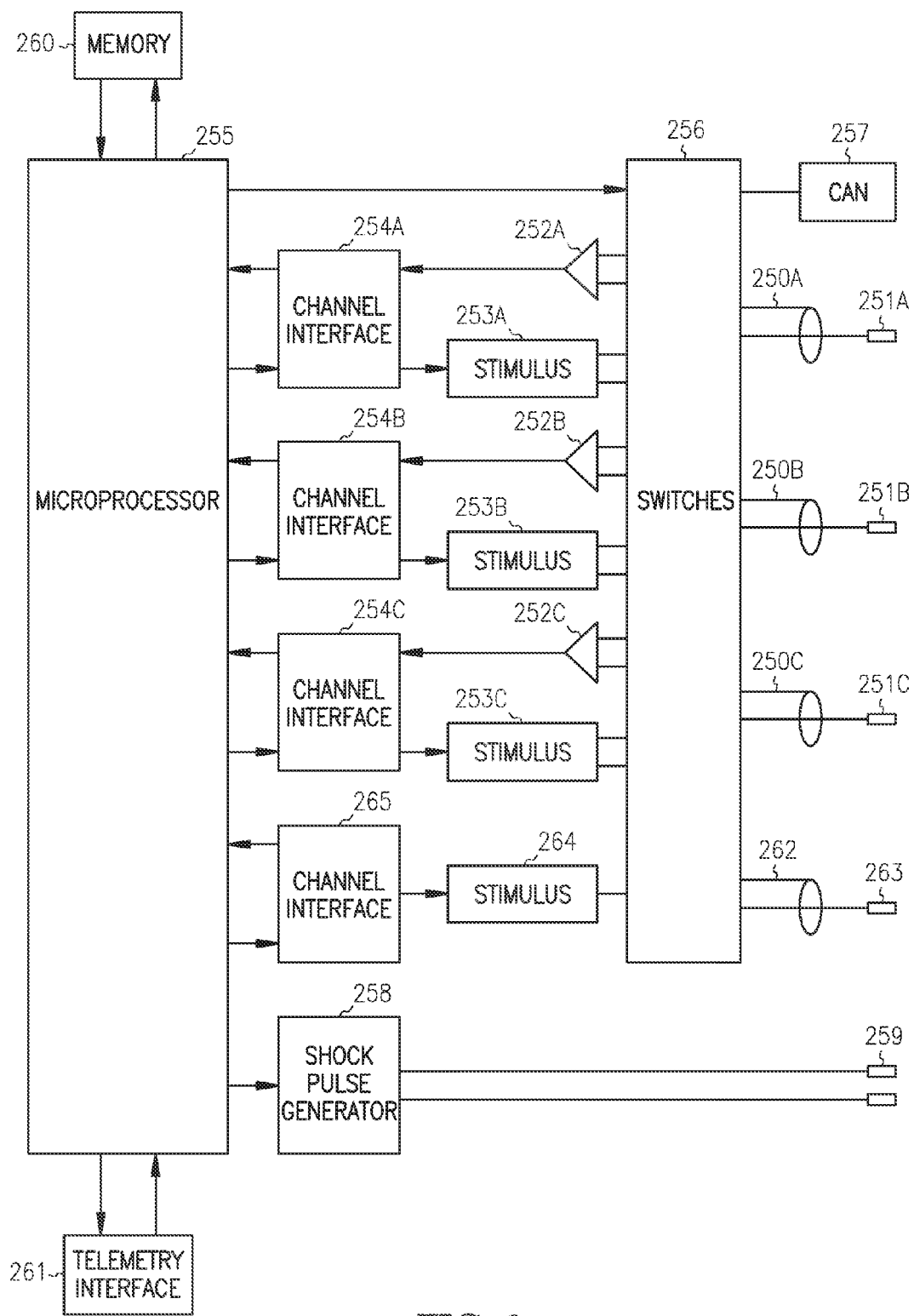
FIG. 3 illustrates a system diagram of an implantable medical device configured for multi-site stimulation and sensing.

FIG. 3 illustrates a system diagram of an implantable medical device embodiment configured for multi-site stimulation and sensing. Three exemplary sensing and pacing channels designated "A" through "C" comprise bipolar leads with ring electrodes 2501-C and tip electrodes 251A-C, sensing amplifiers 2521-C, pulse generators 253A-C, and channel interfaces 254A-C. Each channel thus includes a pacing channel made up of the pulse generator connected to the electrode and a sensing channel made up of the sense amplifier connected to the electrode. The channel interfaces 254A-C communicate bidirectionally with microprocessor 255, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The switching network 256 is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 257 serving as a ground electrode or another electrode on another lead serving as the ground electrode. A shock pulse generator 258 is also interfaced to the controller for delivering a defibrillation shock via a pair of shock electrodes 259 to the atria or ventricles upon detection of a shockable tachyarrhythmia.

The controller or microprocessor controls the overall operation of the device in accordance with programmed instructions stored in memory 260, including controlling the delivery of paces via the pacing channels, interpreting sense signals received from the sensing channels, and implementing timers for defining escape intervals and sensory refractory periods. The controller is able to determine refractory periods for both intrinsic events and paced events. The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. CRT is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites. A telemetry interface 261 is also provided which enables the controller to communicate with an external programmer or remote monitor. According to embodiments of the present subject matter, the implantable medical device tracks the atrial rate, switching modes upon the occurrence of a SVT to block AV conduction and provide bradycardia life support pacing to the ventricle.

Neural stimulation channels are incorporated into the device for delivering neural stimulation to the IVC-LA fat pad, where one channel includes a bipolar lead with a ring electrode 262 and a tip electrode 263, a pulse generator 264, and a channel interface 265. Other embodiments may use unipolar leads in which case the neural stimulation pulses are referenced to the can or another electrode. The pulse generator for each channel outputs a train of neural stimulation pulses which may be varied by the controller as to amplitude, frequency, and duty-cycle. Some embodiments time the delivery of the neural stimulation to the IVC-LA fat pad with a ventricular refractory period (either a sensed intrinsic or paced ventricular beat) to avoid collateral stimulation of the myocardium. The delivery of the neural stimulation can be controlled (reduced or terminated) based on the ventricular refractory period to avoid capturing ventricular tissue with the neural stimulation.

Figure 4A:
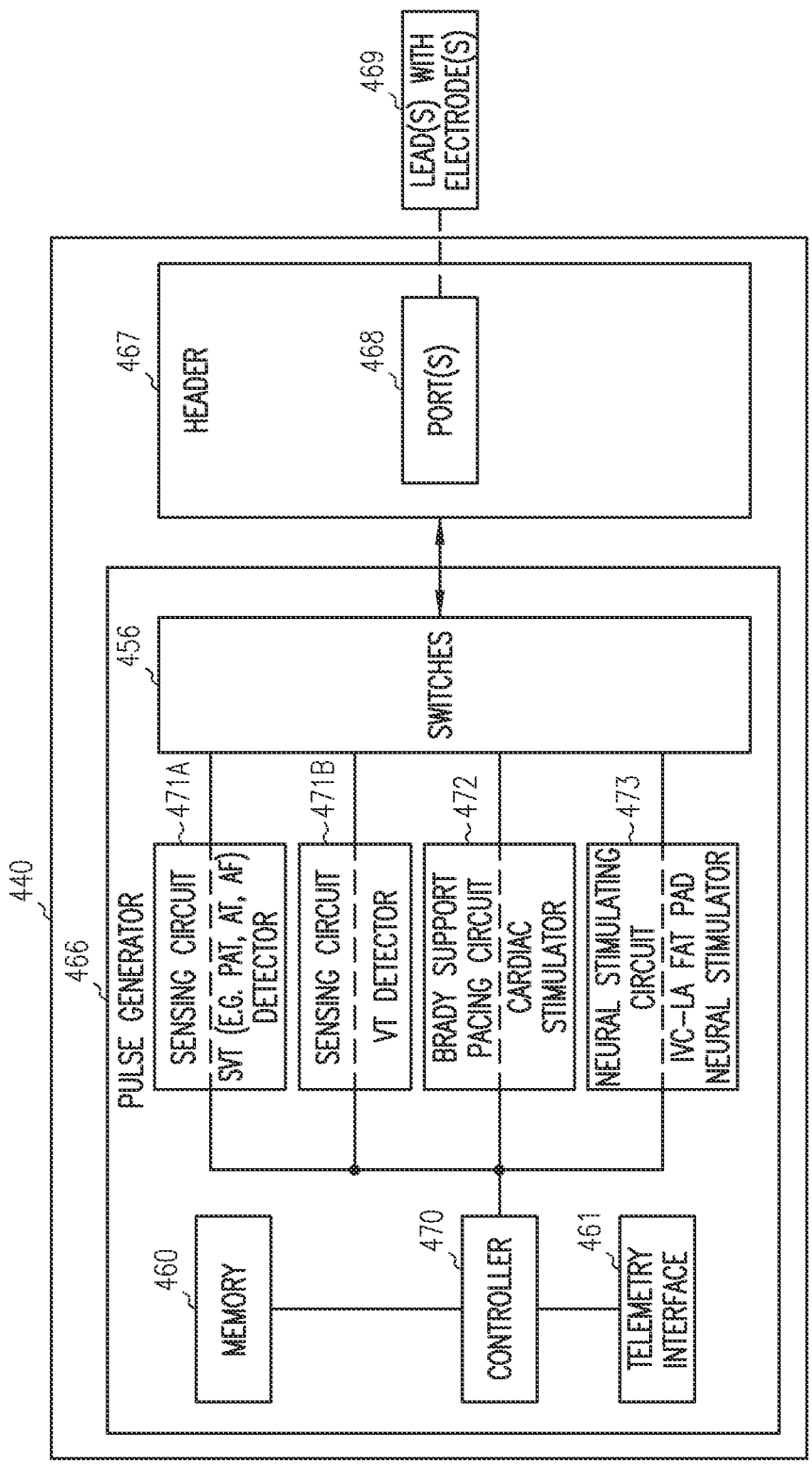
FIGS. 4A and 4B schematically illustrates various embodiments of an implantable medical device used to detect an AVCVT, apply neural stimulation to the IVC-LA fat pad to selectively block the AV conduction and terminate the AVCVT, and provide bradycardia support pacing when the neural stimulation is applied.
Figure 4B:
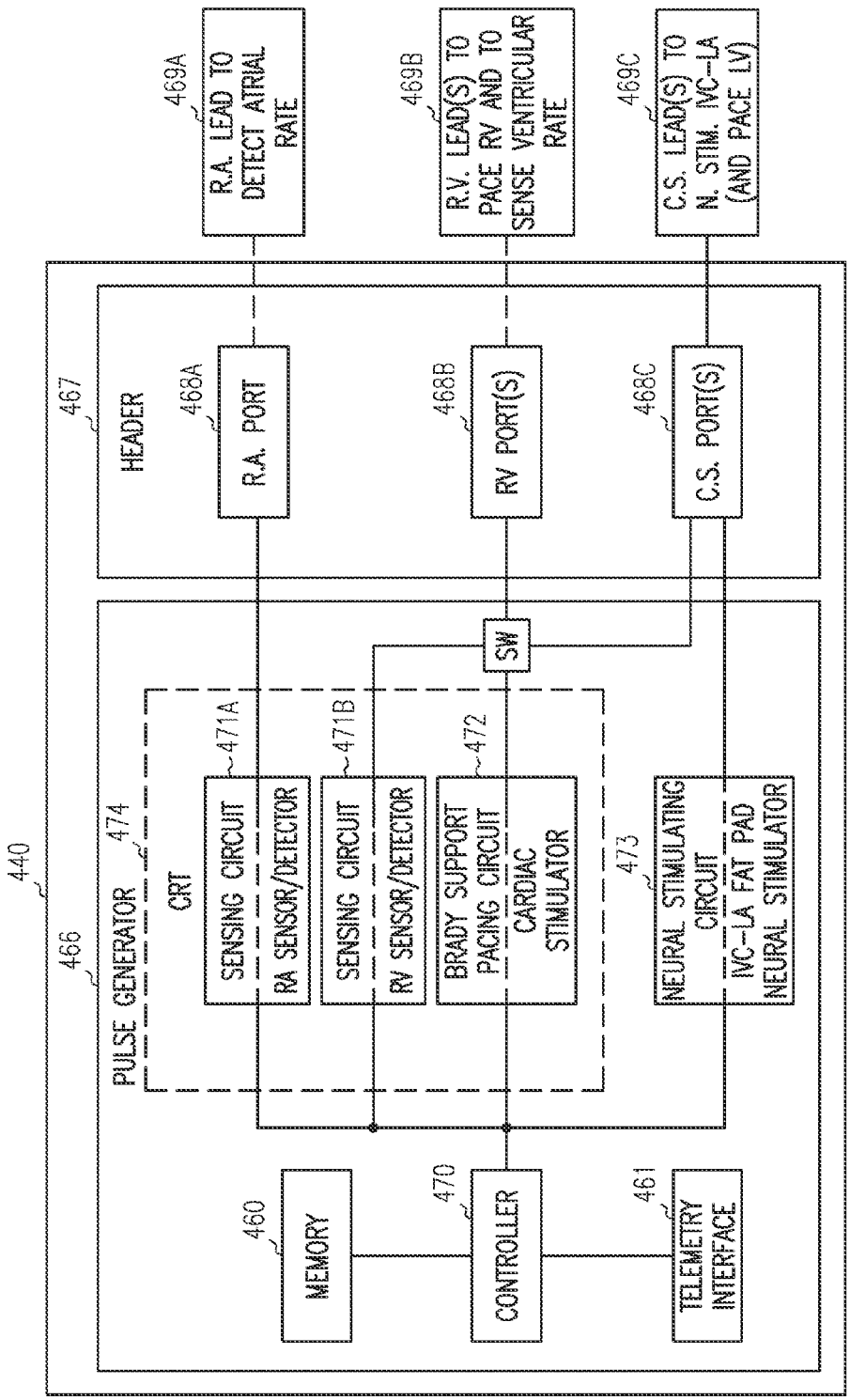

FIGS. 4A and 4B schematically illustrates various embodiments of an implantable medical device used to detect an AVCVT, apply neural stimulation to the IVC-LA fat pad to selectively block the AV conduction and terminate the AVCVT, and provide bradycardia support pacing when the neural stimulation is applied. The illustrated medical devices of FIGS. 4A-4B include pacing and sensing channels, as generally illustrated in FIG. 3, but are illustrated with functional blocks to further illustrate the present subject matter.

FIG. 4A illustrates an implantable medical device, such as can be used for the devices illustrated in FIGS. 2A and 2B. The illustrated device 440 includes a pulse generator 466 and a header 467. The header 467 includes at least one port 468 to receive at least one lead 469 that has at least one electrode. The header 467 functions as an interface between the lead(s) 469 and the pulse generator 466. The illustrated pulse generator includes a controller 470 connected to a memory 460 and a telemetry interface 461 to communicate with an external programmer. The controller 470 is connected to a sensing circuit 471A that functions as a SVT detector (a detector capable of detecting an SVT event such as PAT, AT, AF that induced VT through AV conduction), a sensing circuit 471B that functions as a ventricular rate detector, a cardiac stimulator 472 that cooperates with the ventricular rate sensing circuit 471B and functions as a bradycardia support pacer, and a neural stimulating circuit 473 that functions as an IVC-LA fat pad neural stimulator.

In various embodiments, a VT detector 471B provides ventricular rate feedback. The ventricular rate feedback can be used to provide closed loop control of the neural stimulation to the IVC-LA fat pad. The VT detector 471B in cooperation with the detector 471A is able to detect when a VT is triggered by an SVT event through AV conduction. For example, the SVT detector 471B is used to titrate the neural stimulation therapy to block the AV conduction. If the intrinsic ventricular rate falls below the minimum threshold such as occurs during an AV block, the bradycardia support pacing circuit 472 provides demand pacing to maintain at least the minimum threshold for the ventricular rate.

In some embodiments where it is determined that the applied neural stimulation is capable of capturing ventricular tissue, the controller 470, neural stimulating circuit 473, bradycardia support pacing circuit 472 and sensing circuit 471B cooperate with each other to determine when a ventricular refractory period is occurring, and to time the delivery of the neural stimulation to block the AV conduction during the refractory period. The controller 470 and neural stimulating circuit 473 cooperate to apply neural stimulation to selectively gate the AV conduction. According to these embodiments, when the controller 470 and sensing circuit 471B determine the refractory period is complete or almost complete, the controller 470 and neural stimulating circuit 473 cooperate to temporarily reduce or terminate the neural stimulation to prevent capturing ventricular tissue. The reduced or terminated neural stimulation increases conduction through the AV node. If an intrinsic ventricular event is detected during the time without the AV conduction block, neural stimulation is again applied during the subsequent refractory period. Else, a ventricular pace is provided after an escape interval as part of the bradycardia support pacing therapy, and neural stimulation is applied during the subsequent refractory period.

The SVT detector (e.g. PAT sensor), VT detector, bradycardia support pacer and IVC-LA fat pad neural stimulator appropriately interface with the electrode(s) on the lead(s) via switches 456 (e.g. MOS switches). The switches provide logical connections that allow circuits 471A, 471B, 472, and 473 to connect to a desired port 468 to access a desired electrode channel on a desired lead. FIG. 4A illustrates circuits 471A, 471B, 472, and 473 as being distinct from controller 470. As will be understood by those of ordinary skill in the art upon reading and comprehending this disclosure, various functions associated with circuits 471A, 471B, 472, and 473 can be integrated with controller 470 in various embodiments. The controller 470 is adapted to determine an SVT (e.g. PAT) event from an intrinsic signal sensed by the SVT detector 471A, apply the neural stimulation signal to the IVC-LA fat pad during SVT event using the neural stimulator 473 to block AV conduction and during the SVT event to terminate the AVCVT, and provide bradycardia support pacing using the cardiac stimulator 472 when the neural stimulation signal is applied to the IVC-LA fat pad. Blocking the AV conduction can also serve to terminate AVNRT/PAT.

FIG. 4B illustrates an implantable medical device 440 such as can be used for the device illustrated in FIG. 2B to treat PAT and to provide CRT. For the sake of clarity, FIG. 4B illustrates connections between circuits 471A, 471B, 472, and 473 to ports 468A, 468B and 468C. A switch (SW) is generally illustrated proximate to the bradycardia support pacing circuit 472. The illustrated switch is capable of providing the desired connections, and disconnects, between the circuits 471B and 472 and the ports 468B and 468C to perform the functions provided below. FIG. 4B illustrates a CRT module 474, which includes sensing and stimulating capabilities. In the illustrated embodiment, the CRT module includes a right atrium sensor 471A for use in determining PAT or other SVT, a right ventricular sensor to detect ventricular rate to determine AVCVT triggered by PAT or other SVT, and a bradycardia support pacer 472 used in conjunction with the right ventricular sensor to provide support pacing. According to various embodiments, the PAT detector and bradycardia support pacer are integrated with the sensors and stimulators used by the CRT module.

In the illustrated embodiment, the right atrium sensor/detector 471A is logically connected to a right atrium port 468A to receive a right atrium lead 469A to be placed in the right atrium. The right atrium sensor/detector is adapted to determine an atrial rate from an intrinsic signal received by an electrode on the right atrium lead. The atrial rate is used to determine if a SVT event has taken place. The right ventricle sensor/detector 471B is logically connected to a right ventricle port 468B to receive a right ventricle lead 469B to be placed in the right ventricle. The right ventricle sensor/detector is adapted to determine a ventricular rate from an intrinsic signal received by an electrode on the right ventricle lead. Some embodiments compare the ventricular rate to the atrial rate to verify that a ventricular tachyarrhythmia is attributable to an SVT conducted through the AV node. In various embodiments, the ventricular rate is used to provide closed-loop control of the neural stimulating circuit to block AV conduction, and further is used to provide feedback to pace the right ventricle as part of bradycardia support pacing. FIG. 4B illustrates the bradycardia support pacer 472 connected to both a right ventricle port 468B and at least one coronary sinus port 468C, and further illustrates the IVC-LA fat pad neural stimulator 473 connected to the coronary sinus port(s) 468C. The right ventricle port 468B is adapted to receive a lead 469B with at least one electrode to sense and pace the right ventricle. The coronary sinus port(s) 468C is adapted to receive at least one lead 469C with at least one electrode to be fed through the coronary sinus, to apply a neural stimulation signal to the IVC-LA fat pad and to sense and pace the left ventricle. Various embodiments include one coronary sinus port to receive one lead to be intravascularly fed into the coronary sinus; and various embodiments include two coronary sinus ports to receive one lead intravascularly fed into the coronary sinus for use to apply a neural stimulation signal to the IVC-LA fat pad and another lead intravascularly fed into the coronary sinus for use to sense and pace the left ventricle.

Figure 5:
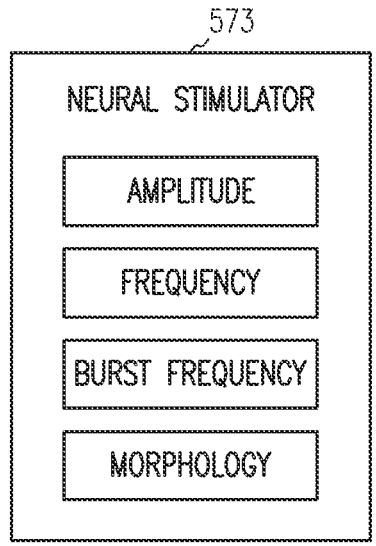
FIG. 5 schematically illustrates an embodiment of a neural stimulator, such as can be implemented at 473 FIGS. 4A and 4B.

FIG. 5 schematically illustrates an embodiment of a neural stimulator 573, such as can be implemented at 473 in FIGS. 4A and 4B. The illustrated neural stimulator embodiment is adapted to adjust the intensity of the applied neural stimulation to the IVC-LA node to further inhibit AV node conduction if appropriate to AVCVT, and in some embodiments to terminate AVNRT. Thus, for example, if a 10 V, 30 Hz, 0.5 ms neural stimulation signal is unsuccessful in terminating the SVT, the neural stimulation signal is adjusted. Various embodiments adjust the amplitude of the signal to increase the neural stimulation and further inhibit the AV node conduction. Various embodiments adjust the frequency of the signal to increase the neural stimulation and further inhibit the AV node conduction. Various embodiments adjust the burst frequency of the signal to increase the neural stimulation and further inhibit the AV node conduction. Various embodiments adjust the wave morphology (e.g. triangular, sinusoidal, square, white noise) of the signal to increase the neural stimulation and further inhibit the AV node conduction. Various embodiments adjust a combination of two or more of the amplitude, the frequency, the burst frequency and the wave morphology of the signal to increase the neural stimulation and further inhibit the AV node conduction. Functions associated with the neural stimulator can be integrated with the controller.

Figure 6:
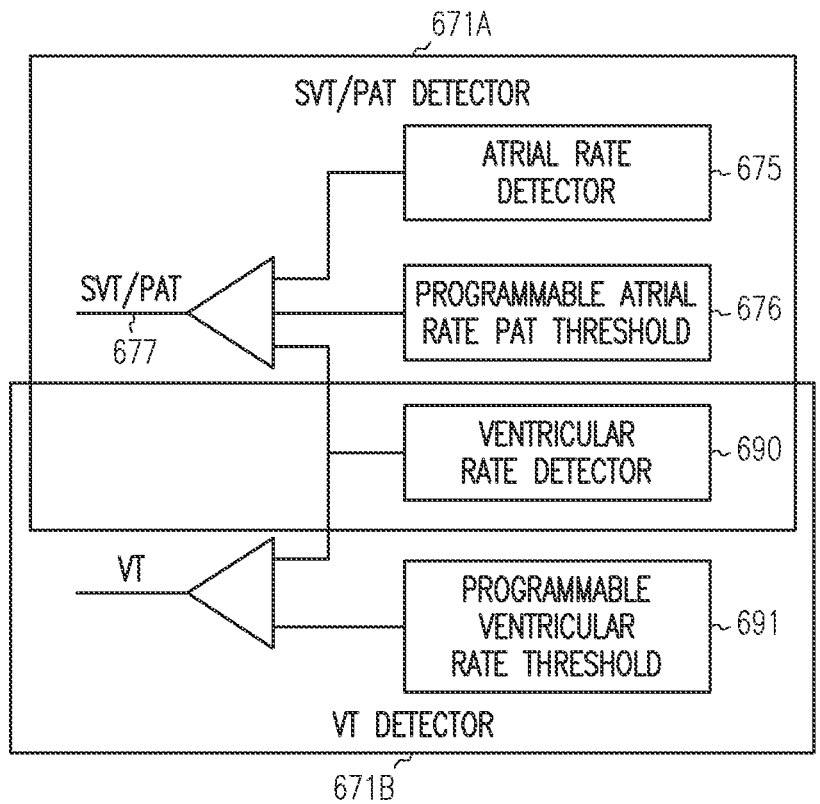
FIG. 6 schematically illustrates logic associated with a SVT detector, such as can be implemented as generally illustrated at 471A in FIGS. 4A and 4B, and further illustrates logic associated with a SVT detector, such as can be implemented as generally illustrated at 471B in FIGS. 4A and 4B, according to various embodiments of the present subject matter.

FIG. 6 schematically illustrates logic associated with a SVT detector, such as can be implemented as generally illustrated at 471A in FIGS. 4A and 4B, and further illustrates logic associated with a SVT detector, such as can be implemented as generally illustrated at 471B in FIGS. 4A and 4B, according to various embodiments of the present subject matter.

Embodiments of the present subject matter are able to selectively turn off and on AV conduction through the selective stimulation of autonomic ganglia in the IVC-LA fat pad. Some embodiments deliver the neural stimulation to the fat pad epicardially, and some embodiments deliver the neural stimulation to the fat pad using transvascular stimulation.

The illustrated PAT detector 671A includes atrial rate detector 675, a ventricular rate detector, and a memory or register 676 for use to store a value corresponding to a programmable PAT atrial rate threshold. The illustrated detector compares the detected atrial rate to the stored threshold value and to the detected ventricular rate, and provides an indication 677 of a PAT event based on the comparison if the rate is higher than the threshold and if the ventricular rate is following the atrial rate, which indicates AVCVT. In various embodiments, the PAT atrial rate threshold is within a range of 160 to 200 beats per minute. Functions associated with the PAT detector can be integrated with the controller.

The illustrated VT detector 671B includes a ventricular rate detector 690 and further includes a memory or register 691 for use to store a value corresponding to a programmable VT threshold. The illustrated VT detector compares the detected ventricular rate to the stored threshold value, and provides an indication of a VT event based on the comparison. Functions associated with the VT detector can be integrated with the controller. In various embodiments, the VT detector and SVT/PAT detector are integrated such that intrinsic signals are sensed from both the right atrium and the right ventricle to determine an occurrence of a PAT event and to determine the efficacy of the neural stimulation therapy. The figure illustrates the ventricular rate detector 696 shared by the SVT/PAT detector 671A and the VT detector 671B.

Figure 7:
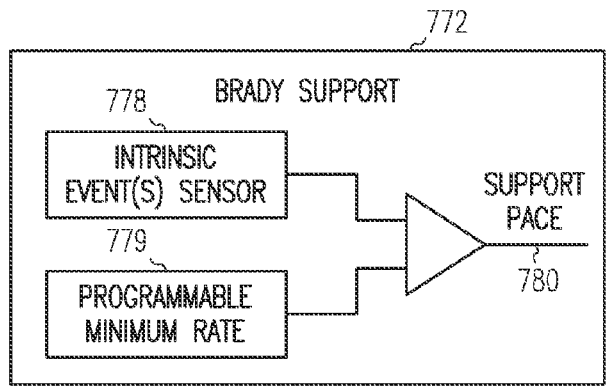
FIG. 7 schematically illustrates logic associated with a bradycardia support pacing circuit, such as can be implemented at 472 in FIGS. 4A and 4B, according to various embodiments of the present subject matter.

FIG. 7 schematically illustrates logic associated with a bradycardia support pacing circuit 772, such as can be implemented at 472 in FIGS. 4A and 4B, according to various embodiments of the present subject matter. The illustrated circuit includes an intrinsic event or events sensor 778, and further includes a memory or register 779 for use to store a value corresponding to a programmable minimum ventricular heart rate or escape interval. The illustrated circuit compares the sensed ventricular rate to the programmable minimum rate or escape interval to provide an indicator 780 to apply a pacing pulse. Functions associated with the bradycardia support pacing circuit can be integrated with the controller.

Figure 8:
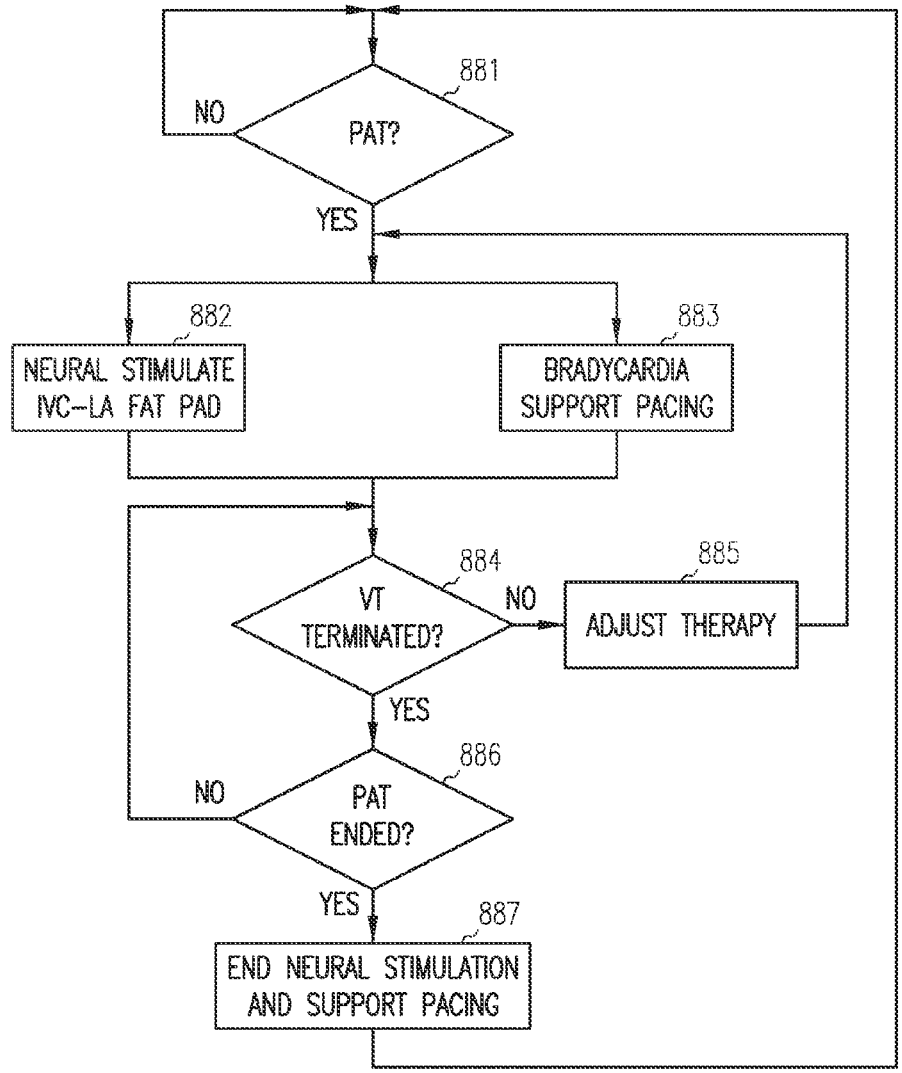
FIG. 8 illustrates a method to treat AVCVT, according to various embodiments of the present subject matter.

FIG. 8 illustrates a method to treat AV-Conducted Ventricular Tachyarrhythmias (AVCVT), according to various embodiments of the present subject matter. The illustrated method is capable of being stored as computer-readable instructions in memory 460 and executed by controller 470 using circuits 471, 472 and 473 in FIGS. 4A-4B, for example. At 881, it is determined if a PAT event (or other AVCVT event) is occurring. If a PAT event is occurring, the process proceeds to 882 to provide neural stimulation to the IVC-LA fat pad and to 883 to provide bradycardia support pacing during the AV conduction block that occurs while the IVC-LA fat pad is being stimulated. Some embodiments control delivery of the neural stimulation based on ventricular refractory period to avoid capturing ventricular tissue with the neural stimulation. The ventricular refractory period can be caused by an intrinsic beat or a ventricular pace. According to various embodiments, it is determined at 884 whether the VT associated with the PAT has been terminated. If the VT has not been terminated, the process proceeds to 885 to adjust the neural stimulation therapy (e.g. amplitude, frequency, burst frequency, and/or wave morphology), and returns to 882 to provide neural stimulation to the IVC-LA fat pad and to 883 to provide bradycardia support pacing during the AV conduction inhibition that occurs while the IVC-LA fat pad is being stimulated. If the VT has terminated, the process proceeds from 884 to 886 to determine if the PAT has ended. The PAT may revert on its own. For AVNRT, the PAT may end based on the neural stimulation, which slows conduction through a feedback path passing through the AV node. If the PAT has not ended, the process proceeds from 886 back to 884 to determine if the VT has been terminated. If the PAT has ended, the process proceeds from 886 to 887 to end the neural stimulation and support pacing, and returns to 881 to determine if a PAT has occurred.

One of ordinary skill in the art will understand that, the modules and other circuitry shown and described herein can be implemented using software, hardware, and combinations of software and hardware. As such, the term module is intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:
1. An implantable medical device, comprising:
 pacing circuitry configured to provide bradycardia support pacing to maintain a minimum heart rate;
 an atrial rate detector configured to detect an atrial rate;

a neural stimulation circuit configured to apply neural stimulation to an interior vena cava-left atrium (IVC-LA) fat pad; and a controller operably connected to the pacing circuitry, the atrial rate detector and the neural stimulation circuit, wherein the controller is configured to control the neural stimulation circuit to deliver neural stimulation to the IVC-LA fat pad on condition that the detected atrial rate exceeds a programmable threshold programmed into the implantable medical device.

2. The device of claim 1, wherein the atrial rate detector is configured to sense an intrinsic signal from a right atrium.

3. The device of claim 1, further comprising a ventricular rate detector configured to detect a ventricular rate.

4. The device of claim 3, wherein the ventricular rate detector is configured to sense an intrinsic signal from the right ventricle.

5. The device of claim 3, wherein the controller is configured to compare the detected ventricular rate and the detected atrial rate, and control the neural stimulator to deliver neural stimulation to the IVC-LA fat pad based on the comparison.

6. The device of claim 5, wherein the controller is configured to control the neural stimulator to deliver neural stimulation to the IVC-LA fat pad on condition that the detected atrial rate exceeds a threshold and the detected ventricular rate follows the detected atrial rate.

7. The device of claim 3 wherein the pacing circuitry is configured to cooperate with the ventricular rate detector to provide ventricular pacing to maintain the detected ventricular rate at or above a minimum ventricular rate.

8. The device of claim 1, wherein the ventricular rate detector is configured to sense an intrinsic signal in a right ventricle, and the pacing circuitry is configured to pacing the right ventricle.

9. The device of claim 1, wherein the controller is adapted to identify a ventricular refractory period and to control delivery of the neural stimulation based on the ventricular refractory period to avoid capturing ventricular tissue with the neural stimulation.

10. The device of claim 1, wherein the neural stimulation circuit includes an epicardial electrode used to apply the neural stimulation to the IVC-LA fat pad.

11. The device of claim 1, wherein the neural stimulation circuit includes an electrode configured for placement in a coronary sinus used to transvascularly apply the neural stimulation to the IVC-LA fat pad.

12. The device of claim 1, wherein the neural stimulation has a frequency of approximately 30 Hz and a duration of approximately 0.05 ms.

13. The device of claim 1, wherein the controller is configured to adjust the neural stimulation if the atrial rate is not reduced by the neural stimulation.

14. An implantable medical device, comprising:
pacing circuitry configured to provide bradycardia support pacing to maintain a minimum heart rate;
an atrial rate detector configured to detect an atrial rate;
a neural stimulation circuit configured to apply neural stimulation to an inferior vena cava-left atrium (IVC-LA) fat pad;
a shockable event detector configured to detect a cardiac event indicated for an electrical shock to terminate the cardiac event; and
a shock pulse generator configured to electrically shock cardiac tissue; and
a controller operably connected to the shockable event detector, the shock pulse generator, the pacing circuitry, the atrial rate detector and the neural stimulation circuit, wherein the controller is configured to:
respond to a detected cardiac event indicated for the electrical shock by controlling the shock pulse generator to electrically shock cardiac tissue; and
control the neural stimulator to deliver neural stimulation to the IVC-LA fat pad on condition that the detected atrial rate exceeds a programmable threshold programmed into the implantable medical device.

15. The device of claim 14, wherein the controller is adapted to identify a ventricular refractory period and to control delivery of the neural stimulation based on the ventricular refractory period to avoid capturing ventricular tissue with the neural stimulation.

16. The device of claim 14, wherein the neural stimulation circuit includes an epicardial electrode used to apply the neural stimulation to the IVC-LA fat pad.

17. The device of claim 14, wherein the neural stimulation circuit includes an electrode configured for placement in a coronary sinus used to transvascularly apply the neural stimulation to the IVC-LA fat pad.

18. An implantable medical device, comprising:
pacing circuitry configured to provide bradycardia support pacing to maintain a minimum heart rate;
an atrial rate detector configured to sense an intrinsic signal from a right atrium to detect an atrial rate;
a ventricular rate detector configured to sense an intrinsic signal from a right ventricle to detect a ventricular rate;
a neural stimulation circuit configured to apply neural stimulation to an inferior vena cava-left atrium (IVC-LA) fat pad;
a shockable event detector configured to detect a cardiac event indicated for an electrical shock to terminate the cardiac event;
a shock pulse generator configured to electrically shock cardiac tissue; and
a controller operably connected to the shockable event detector, the shock pulse generator, the pacing circuitry, the atrial rate detector and the neural stimulation circuit, wherein the controller is configured to:
respond to a detected cardiac event indicated for the electrical shock by controlling the shock pulse generator to electrically shock cardiac tissue;
control the neural stimulation circuit to deliver neural stimulation to the IVC-LA fat pad on condition that the detected atrial rate exceeds a programmable threshold programmed into the implantable medical device and that the detected ventricular rate follows the detected atrial rate; and
adjust the neural stimulation if the atrial rate is not reduced by the neural stimulation.

19. The device of claim 18, wherein the controller is adapted to identify a ventricular refractory period and to control delivery of the neural stimulation based on the ventricular refractory period to avoid capturing ventricular tissue with the neural stimulation.

20. The device of claim 18, wherein the neural stimulation has a frequency of approximately 30 Hz and a duration of approximately 0.05 ms.

* * * * *